United States Patent
Coillard-Lavirotte et al.

(10) Patent No.: US 10,575,888 B2
(45) Date of Patent: Mar. 3, 2020

(54) GRIPPING HANDLE FOR A SURGICAL TOOL, AND METHOD AND MACHINE FOR PRODUCING SUCH A GRIPPING HANDLE

(71) Applicant: IN2BONES, Ecully (FR)

(72) Inventors: Jean-Yves Paul Albert Coillard-Lavirotte, Saint Cyr au Mont d'Or (FR); Daniel Edmond Boublil, Lyons (FR); Philippe Emmanuel D'Ingrado, Saint Didier au Mont d'Or (FR)

(73) Assignee: IN2BONES, Ecully (FR)

( * ) Notice: Subject to any disclaimer, the term of this patent is extended or adjusted under 35 U.S.C. 154(b) by 392 days.

(21) Appl. No.: 15/502,536

(22) PCT Filed: Aug. 7, 2015

(86) PCT No.: PCT/FR2015/052177
§ 371 (c)(1),
(2) Date: Feb. 8, 2017

(87) PCT Pub. No.: WO2016/024063
PCT Pub. Date: Feb. 18, 2016

(65) Prior Publication Data
US 2017/0224399 A1    Aug. 10, 2017

(30) Foreign Application Priority Data

Aug. 13, 2014  (FR) ...................... 14 57781

(51) Int. Cl.
*A61B 17/00* (2006.01)
*A61B 17/88* (2006.01)
(Continued)

(52) U.S. Cl.
CPC .......... *A61B 17/8875* (2013.01); *A61B 17/28* (2013.01); *B25B 15/02* (2013.01);
(Continued)

(58) Field of Classification Search
CPC .. A61B 2017/0046; A61B 2017/00464; A61B 2017/00473; A61B 17/8875;
(Continued)

(56) References Cited

U.S. PATENT DOCUMENTS 2,682,414 A * 6/1954 Richardson ............. B25B 15/02
279/77
5,931,065 A * 8/1999 Jackson .............. B25B 23/0021
81/177.1
(Continued)

OTHER PUBLICATIONS

International Search Report in connection with PCT International Application No. PCT/FR2015/052177.

*Primary Examiner* — Nicholas W Woodall
(74) *Attorney, Agent, or Firm* — John P. White; Cooper & Dunham LLP

(57) ABSTRACT

The invention concerns a gripping handle (1) comprising:
a main body (3),
a receiving orifice (4) formed within the main body (3) for receiving a sliding removable working bit (2),
a blocking lever (14) rotatably mounted on the main body (3) between:
a blocking orientation in which it blocks the sliding of the working bit (2),
a release orientation in which it enables the sliding of the working bit (2),
an elastic pivot (15, 16) designed to bring, by itself, the blocking lever (14) back in the blocking orientation,
the gripping handle (1) being characterized in that the main body (3), the blocking lever (14) and the elastic pivot (15, 16) are integral with each other.
Surgical instrumentation.

27 Claims, 3 Drawing Sheets

(51) Int. Cl.
| | |
|---|---|
| *B25B 23/00* | (2006.01) |
| *B25G 3/04* | (2006.01) |
| *B25G 3/10* | (2006.01) |
| *B25G 3/12* | (2006.01) |
| *B25G 3/18* | (2006.01) |
| *B25G 3/20* | (2006.01) |
| *B25G 3/24* | (2006.01) |
| *B25G 3/28* | (2006.01) |
| *B25B 15/02* | (2006.01) |
| *B25G 1/00* | (2006.01) |
| *B25G 1/06* | (2006.01) |
| *A61B 17/28* | (2006.01) |
| *A61B 17/3211* | (2006.01) |
| *B25G 1/08* | (2006.01) |

(52) U.S. Cl.
CPC ............. *B25G 1/005* (2013.01); *B25G 1/066* (2013.01); *B25G 3/04* (2013.01); *B25G 3/10* (2013.01); *B25G 3/12* (2013.01); *B25G 3/18* (2013.01); *B25G 3/20* (2013.01); *B25G 3/24* (2013.01); *B25G 3/28* (2013.01); *A61B 17/3211* (2013.01); *A61B 2017/0042* (2013.01); *A61B 2017/0046* (2013.01); *A61B 2017/00526* (2013.01); *B25B 23/0042* (2013.01); *B25G 1/085* (2013.01)

(58) Field of Classification Search
CPC ... B25G 3/04; B25G 3/10; B25G 3/12; B25G 3/18; B25G 3/20; B25G 3/24; B25G 3/28; B25B 23/0042
See application file for complete search history.

(56) References Cited

U.S. PATENT DOCUMENTS

| | | | | |
|---|---|---|---|---|
| 6,702,332 | B2* | 3/2004 | Young | A47L 9/242 |
| | | | | 15/327.1 |
| 6,832,784 | B1* | 12/2004 | Chen | A47L 9/244 |
| | | | | 285/303 |
| 7,712,399 | B2* | 5/2010 | Nenadic | B25B 23/0035 |
| | | | | 7/128 |
| 8,485,488 | B2* | 7/2013 | Forrest | A47B 91/02 |
| | | | | 248/188.8 |
| 9,517,550 | B2* | 12/2016 | Palmisano | B25B 23/0035 |
| 2005/0178251 | A1 | 8/2005 | Holland-Letz | |
| 2014/0121694 | A1 | 5/2014 | Lambert | |

* cited by examiner

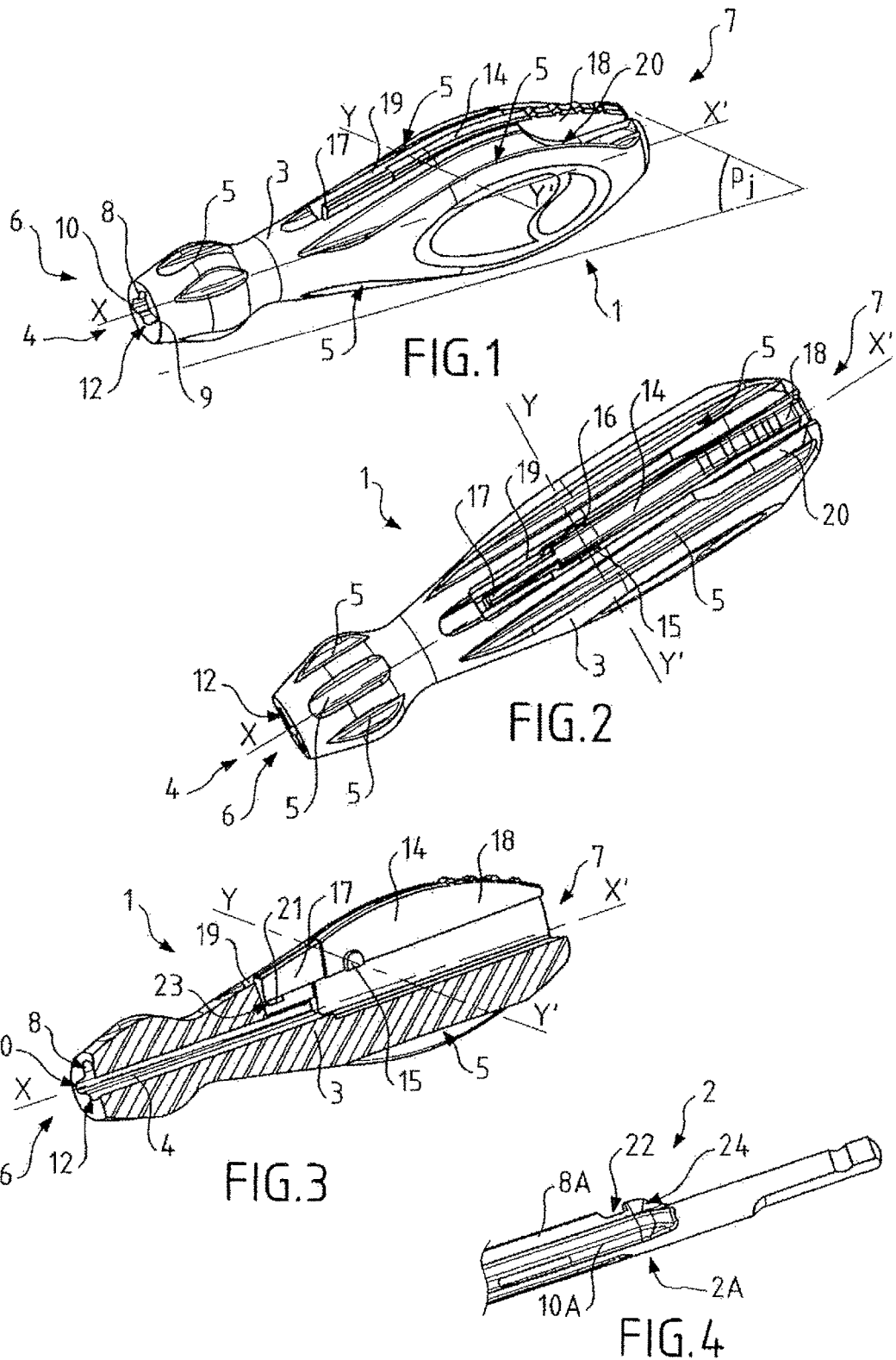

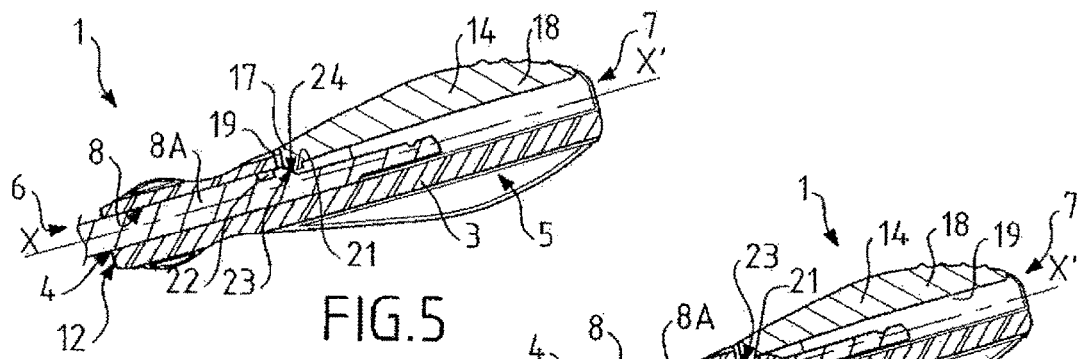
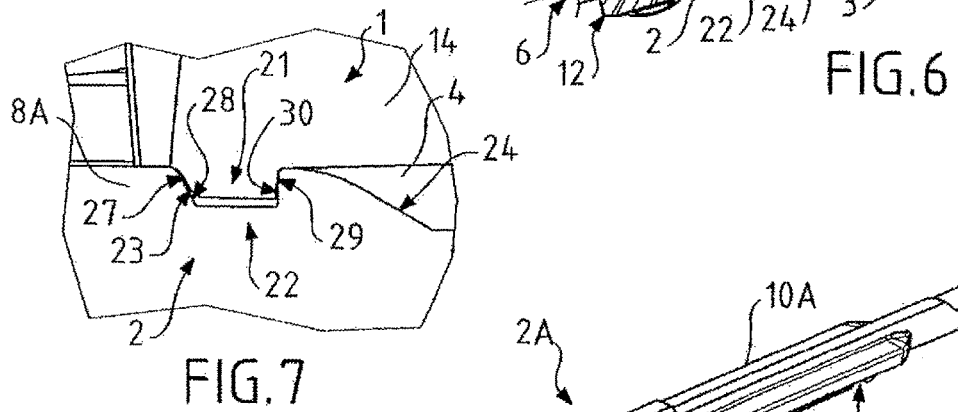
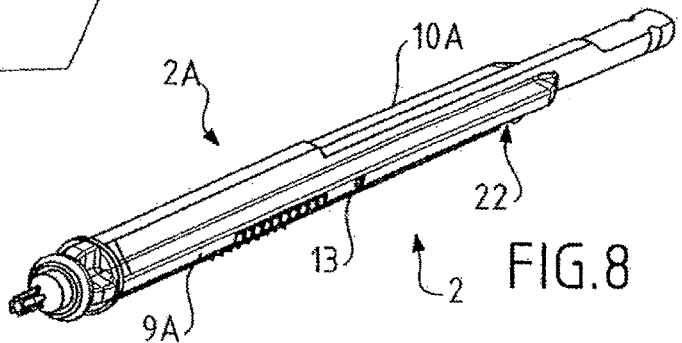
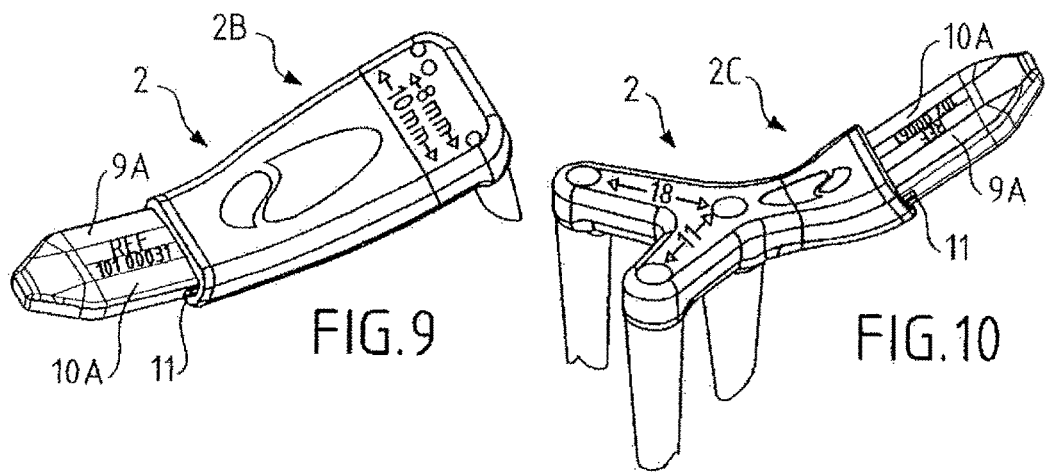

GRIPPING HANDLE FOR A SURGICAL TOOL, AND METHOD AND MACHINE FOR PRODUCING SUCH A GRIPPING HANDLE

CROSS-REFERENCE TO RELATED APPLICATIONS

This application is a § 371 national stage of PCT International Application No. PCT/FR2015/052177, filed Aug. 7, 2015, claiming priority of French Patent Application No. FR 1457781, filed Aug. 13, 2014, the content of each of which is hereby incorporated by reference into the application.

TECHNICAL FIELD

The present invention concerns the field of surgical instrumentation, in particular surgical tools with removable or interchangeable handles, such as surgical screwdrivers with bits.

More specifically, the invention concerns a gripping handle designed to receive a removable working bit in order to form a surgical tool with the latter, said gripping handle comprising:
- a main body extending along a longitudinal axis between a proximal end and a distal end,
- a receiving orifice formed within the main body and being designed to slidingly receive the working bit,
- a lever for blocking the sliding of the working bit in the receiving orifice, the blocking lever being rotatably mounted on the main body about an axis of rotation so as to be able to tilt between:
- a blocking orientation in which said lever blocks the sliding of the working bit,
- a release orientation in which it enables the sliding of the working bit in the receiving orifice,
- an elastic pivot by which the blocking lever is rotatably mounted on the main body, the elastic pivot being designed to bring, by itself, the blocking lever back in the blocking orientation when the latter is in the release orientation.

The invention also concerns a surgical tool kit comprising a gripping handle.

The invention further concerns a method for manufacturing a gripping handle.

The invention finally concerns a manufacturing machine.

PRIOR ART

In the field of surgical instrumentation, there are known modular surgical screwdrivers, with interchangeable bits. Thus, equipped with one single screwdriver handle and with a plurality of screwdriver bits with different functions, a surgeon can face a multitude of surgical situations.

For these known modular screwdrivers, during the assembly of the handle with a given bit, this assembly should be particularly reliable and solid, in particular in order that no risk of accidental detachment of the bit subsists, and in order that the clearance between the handle and said bit remains reduced to a minimum, considering the accuracy required for the surgical gestures.

Consequently, these known screwdrivers are generally manufactured using parts with high accuracy, and which undergo a complex and accurate assembly in order to form the handle of a screwdriver presenting the required qualities, so that they are relatively expensive and difficult to manufacture. Moreover, the necessity to clean and sterilize the surgical instrumentation between each operation is likely to deteriorate, more or less progressively, this assembly, so that the known tool may present a clearance, or a progressive wear.

For known modular screwdrivers, securing a given bit to the removable handle may be performed by actuating a movable part of the handle, for example a button or a rotating lever. The wear of such parts may possibly result in making their actuation inconvenient, or on the contrary too flexible, so that the change of the bit is likely to become difficult over time, which is likely to cause a substantial loss of time during a surgical operation, or on the contrary too loose, so as to increase the risk of accidental detachment of the bit.

DISCLOSURE OF THE INVENTION

Consequently, the objects assigned to the present invention aim to remedy to the different drawbacks enumerated hereinbefore and to propose a new gripping handle, a new surgical tool kit, a new manufacturing method and a new manufacturing machine, allowing a particularly rapid and inexpensive manufacture.

Another object of the invention aims to propose a new gripping handle, a new surgical tool kit, a new manufacturing method and a new manufacturing machine allowing forming a particularly reliable and robust surgical tool.

Another object of the invention aims to propose a new gripping handle, a new surgical tool kit, a new manufacturing method and a new manufacturing machine, allowing forming a gripping handle the use of which is particularly easy and comfortable.

Another object of the invention aims to propose a new gripping handle, a new surgical tool kit, a new manufacturing method and a new manufacturing machine, allowing forming a gripping handle which is particularly easy to manufacture.

Another object of the invention aims to propose a new gripping handle, a new surgical tool kit, a new manufacturing method and a new manufacturing machine, allowing forming a removable gripping handle intended to belong to a surgical tool presenting a high accuracy and substantially devoid of any mounting clearance.

Another object of the invention aims to propose a new gripping handle and a new surgical tool kit allowing guaranteeing a good sterilization of the surgical environment.

The objects assigned to the invention are achieved by means of a gripping handle designed to receive a removable working bit in order to form a surgical tool with the latter, said gripping handle comprising:
- a main body extending along a longitudinal axis between a proximal end and a distal end,
- a receiving orifice formed within the main body and being designed to slidingly receive the working bit,
- a lever for blocking the sliding of the working bit in the receiving orifice, the blocking lever being rotatably mounted on the main body about an axis of rotation so as to be able to tilt between:
- a blocking orientation in which said lever blocks the sliding of the working bit,
- a release orientation in which it enables the sliding of the working bit in the receiving orifice,
- an elastic pivot by which the blocking lever is rotatably mounted on the main body, the elastic pivot being designed to bring, by itself, the blocking lever back in the blocking orientation when the latter is in the release orientation, the gripping handle being characterized in that the main body, the blocking lever and the elastic pivot are integral with each other so as to form a one single-piece part.

The objects assigned to the invention are also achieved by means of a surgical tool kit comprising a gripping handle according to the invention, as well as at least one removable working bit, preferably two removable working bits having different functions.

The objects assigned to the invention are further achieved by means of a method for manufacturing a gripping handle according to, the invention, the manufacturing method being characterized in that it comprises one single molding step during which the gripping handle is made in one piece in its entirety.

Finally, the objects assigned to the invention are achieved by means of a machine for manufacturing a gripping handle allowing implementing the manufacturing method of the invention.

BRIEF DESCRIPTION OF THE DRAWINGS

Other particularities and advantages of the invention will appear and come out in more details upon reading the description made hereinafter, with reference to the appended drawings, given only as an illustrative and non-limiting example, in which:

FIG. 1 illustrates, according to a general perspective view, a gripping handle according to the invention, FIG. 2 represents, according to a general top perspective view, the gripping handle of FIG. 1, FIG. 3 illustrates, according to a perspective longitudinal sectional view, the gripping handle of FIGS. 1 and 2, FIG. 4 illustrates, according to a partial perspective view, a removable working bit according to the invention, intended to be assembled with the gripping handle of FIGS. 1 to 3 so as to form a surgical tool, FIGS. 5 and 6 illustrate, according to perspective longitudinal sectional views, the gripping handle of FIGS. 1 to 3 associated with the removable working bit of FIG. 4, FIG. 7 represents a detail of the realization of the gripping handle of FIGS. 1 to 3, FIG. 8 represents a general perspective view of the working bit of FIGS. 4 to 6, FIGS. 9 and 10 each illustrate a general perspective view of a distinct variant of the working bit associable to the gripping handle of FIGS. 1 to 7.

BEST MODE FOR CARRYING OUT THE INVENTION

Figure 11:
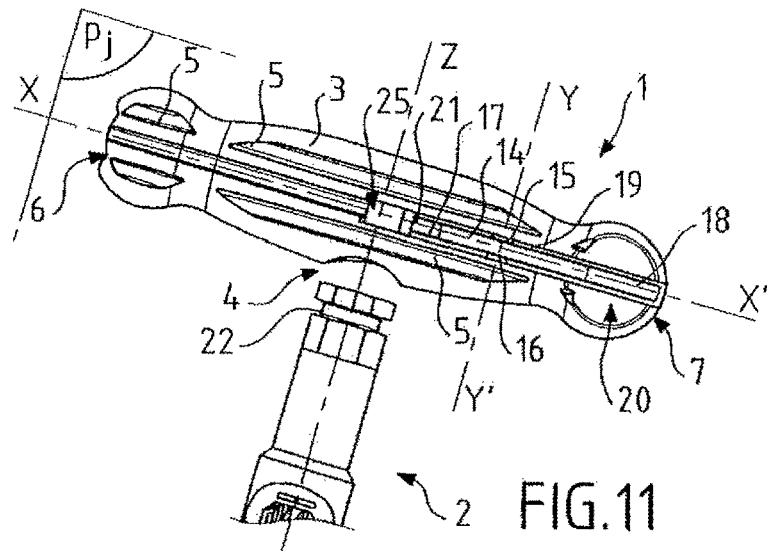
FIG. 11 illustrates, according to an exploded side perspective view, another variant of a gripping handle and of a working bit in accordance with the invention.
Figure 12:
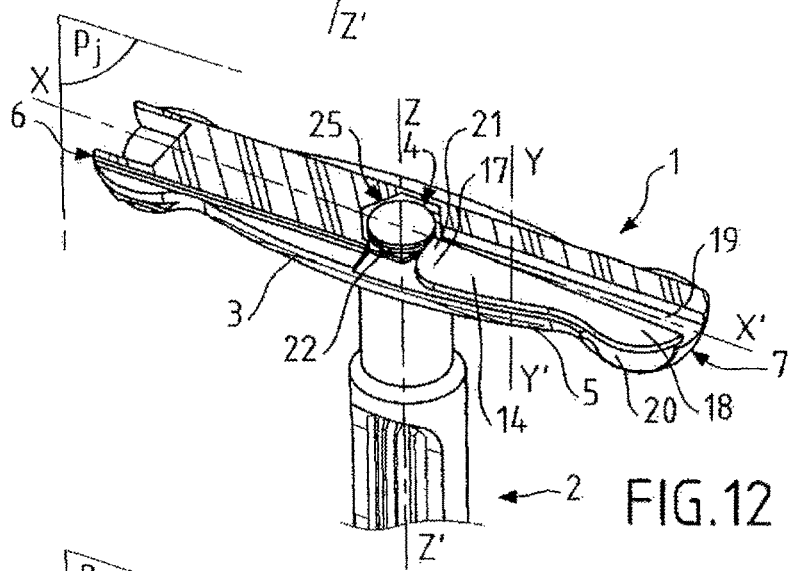
FIGS. 12 and 13 illustrate, according to perspective views, the gripping handle and the working bit of FIG. 10, the gripping handle having been cut longitudinally.
Figure 13:
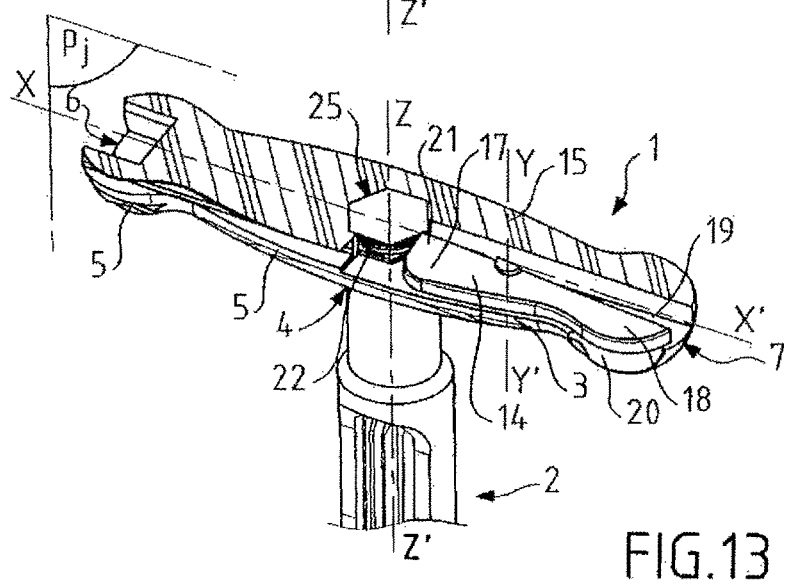

The invention concerns a part intended to participate in forming a demountable and modular surgical tool, and in this case, it concerns a gripping handle 1 of the surgical tool a first embodiment of which in accordance with the invention is illustrated in FIGS. 1 to 3, and a second embodiment in accordance with the invention is illustrated in FIGS. 11 to 13.

The gripping handle 1, which in other terms constitutes a grip or still a gripping pommel, is designed, according to the invention, to receive a removable working bit 2 in order to form a surgical tool with the latter, that is to say, in this case, a surgical instrument particularly adapted to be used by a surgeon during a surgical operation on a patient. Of course, without departing from the scope of the invention, the gripping handle 1 and the surgical tool that it participates to form may be used in the context of an animal surgery, or for uses other than surgery, for example for screwing a screw within a non-living mechanism.

The gripping handle 1 of the invention constitutes an area of the formed surgical tool which may be conveniently grasped by the surgeon, for example with one hand, or with two. In turn, the working bit 2 forms the functional portion of the tool, and advantageously constitutes a means for action, for example mechanical, on the body of the patient, or on another object, for example a screw or a staple. Advantageously, the surgical instrument formed thereby may be used by the surgeon, depending on the working bit 2 received by the gripping handle 1, to perform:

screwing or unscrewing of a screw, for example an osteosynthesis screw, or setting of an osteosynthesis staple, in the body of a patient.

In order to perform the previous actions, the surgeon can use several distinct variants of working bits, in particular:

a working bit 2 forming a screwdriver bit 2A, that is to say a screwdriver axis (as illustrated in FIG. 8), a working bit 2 forming a wires setting guide 2B (as illustrated in FIG. 9), a working bit 2 forming a drill guide 2C for setting a staple (as illustrated in FIG. 10), a working bit 2 forming a scalpel blade (not represented).

In turn, the gripping handle 1 advantageously forms a screwdriver handle, and/or a handle for supporting a wires setting guide and/or a drill guide, and/or a scalpel handle. Preferably, the gripping handle 1 is multifunction and versatile, and is adapted to receive working bits 2 with various and distinct functions.

The gripping handle 1 of the invention comprises a main body 3 extending along a longitudinal axis X-X' between a proximal end 7 and a distal end 6. Advantageously, the main body 3 presents an axial or elongate general shape, preferably a general form of revolution about a longitudinal axis X-X', so as to be adapted to be handled by the surgeon in an ergonomic and safe manner.

Preferably, the main body 3 presents the shape of a conventional screwdriver handle, as illustrated for example in FIGS. 1 to 3, but may alternatively present the shape of a pommel or of a grip, as illustrated for example in FIGS. 11 to 13.

In the preferred example illustrated in FIGS. 1 to 3, preferably, the proximal end 7 is intended to form the back of the surgical tool, and more specifically the end of the tool which is intended to be turned in the direction of the surgeon. In turn, the distal end 6 will advantageously be intended to be turned in the direction of the patient. Thus, the formed surgical tool will preferably be a straight axial tool.

In the preferred second example illustrated in FIGS. 11 to 13, the gripping handle 1 may for example serve to form a bent or «T»-shaped tool, the working bit 2 then extending perpendicularly to the gripping handle 1, so that the distal end 6 and the proximal end 7 form a straight and skewed portion of the gripping handle 1 of the tool, which is for example intended to be disposed transversely with respect to the patient.

In the preferred case where the gripping handle 1 is intended to form the handle of a screwdriver, it will be intended to be rotated about its longitudinal axis X-X' in order to screw or unscrew a screw by means of the working bit 2. In this preferred case, or in every other case, the gripping handle 1 presents a distal portion the general shape of which is an ellipsoid of revolution, the diameter of revolution of which is coaxial with the longitudinal axis X-X'. Such a shape is particularly adapted to grasp for rotation about the longitudinal axis X-X', as illustrated in the figures.

Preferably, the gripping handle 1 may present an antiskid external surface. In particular, the gripping handle 1 may present furrows 5, for example parallel to each other, formed in the main body 3 along the latter, according to a longitudinal direction. Advantageously, these furrows 5 have the triple function of improving the adherence of gripping, lightening the main body 3 so as to save weight and matter, and allowing realizing the main body 3 by molding. Indeed, the furrows 5 are preferably deep enough so that the main body 3, while presenting an ergonomic external contour, for example having the shape of a conventional screwdriver handle, is substantially devoid of any areas where the matter is very thick, in order to minimize shrinkage when demolding. In addition, the furrows 5 are disposed in the main body 3 so that the latter could be demolded during its manufacture, around a parting plane $P_j$ including for example the longitudinal axis X-X'. To this end, the furrows 5 are advantageously orientated according to planes orthogonal to said parting plane $P_j$, parallel to the longitudinal axis X-X', and are for example set back with respect to the latter.

According to the invention, the gripping handle 1 also comprises a receiving orifice 4 formed within the main body 3 and being designed to slidingly receive the working bit 2. Thus, the gripping handle 1 includes a receiving orifice 4 within which the working bit 2 may be assembled to the gripping handle 1. The shape, and especially the section of the receiving orifice 4 is advantageously shaped so as to fit with the working bit 2, so that the gripping handle 1 forms the female portion of the surgical tool, the working bit 2 forming the male portion.

In the case of FIGS. 1 to 3, the receiving orifice 4 is advantageously formed within the main body 3 from the distal end 6 so as to form an axial surgical tool. In this case, the receiving orifice 4 is preferably designed to receive the working bit 2 slidingly along the longitudinal axis X-X', so as to form an axial surgical tool.

The gripping handle 1 is designed so that the working bit 2, being inserted in the receiving orifice 4, could translate within the latter in the direction of the length of the main body, throughout a limited or non-limited stroke. Thus, the receiving orifice 4 forms a rail, or still a sliding guide of the working bit 2 along the longitudinal axis X-X'.

Preferably, as illustrated in FIGS. 1 to 3, the receiving orifice 4 is formed within the main body 3 from the distal end 6, for example in alignment with the longitudinal axis X-X'. Of course, it is still possible to form the receiving orifice 4 from the lateral surface of the main body 3, or offset with respect to the longitudinal axis X-X'. Optionally, the receiving orifice 4 passes throughout the main body 3, for example from the distal end 6 to the proximal end 7, which in particular allows facilitating the manufacture of the gripping handle 1.

Alternatively, in the preferred case represented for example in FIGS. 11 to 13, the receiving orifice 4 is formed within the main body 3, so as to open from the outer surface of the latter, between the distal end 6 and the proximal end 7. Thus, the receiving orifice 4 is preferably located on an intermediate portion of the gripping handle 1, and is preferably located halfway, medially, between the proximal end 7 and the distal end 6.

Advantageously, the receiving orifice 4 is designed, in this case, to receive the working bit 2 slidingly along an orthogonal axis Z-Z' orthogonal to the longitudinal axis X-X' so as to form a «T»-shaped surgical tool.

Preferably, the receiving orifice 4 presents a shape congruent with the external contour of the working bit 2, and allows blocking the rotation of the working bit 2 relative to said gripping handle 1 respectively about the longitudinal axis X-X' for the preferred variant of FIGS. 1 to 3, or about the orthogonal axis Z-Z' for the preferred variant of FIGS. 11 to 13, while enabling the sliding of said working bit 2 relative to the gripping handle 1 along the same axis.

In order to allow driving the working bit 2 in rotation by the gripping handle 1 respectively about the longitudinal axis X-X', or the orthogonal axis Z-Z', the receiving opening 4 presents, over at least a portion of its depth, a shape which advantageously is not a form of revolution respectively about the longitudinal axis X-X', or the orthogonal axis Z-Z'.

Preferably, in particular in the preferred case represented in FIGS. 1 to 3, the receiving orifice 4 presents a section the shape of which allows blocking the rotation of the working bit 2 relative to said gripping handle 1 about the longitudinal axis X-X', while enabling the sliding of said working bit 2 relative to the gripping handle 1 along the longitudinal axis X-X'. Thus, according to this configuration, the receiving orifice 4 allows substantially only one degree of freedom to the working bit 2 when the latter is inserted within said receiving orifice 4.

To this end in particular, the receiving orifice 4 presents at least one main longitudinal slot 8 extending over at least a portion of the length of said receiving orifice 4, the main longitudinal slot 8 being designed to cooperate with a main longitudinal fin 8A of the working bit 2 in order to rotatably secure said working bit 2 relative to said gripping handle 1 about the longitudinal axis X-X' (as illustrated in FIGS. 1 to 3). Thus, preferably, during the rotation about the longitudinal axis X-X' of the gripping handle 1 of the formed surgical tool, the main longitudinal slot 8 drives mechanically in rotation the main longitudinal fin 8A, which has a complementary shape, while coming into contact with the latter. For example, the main longitudinal slot 8 extends radially from the longitudinal axis X-X', along a plane which is orthogonal to the parting plane $P_j$ and at the same time comprises the longitudinal axis X-X'.

Preferably, the receiving orifice 4 also presents two appended longitudinal slots 9, 10 disposed symmetrically with respect to a plane formed by the main longitudinal slot 8, the appended longitudinal slots 9, 10 being designed to cooperate each with an appended longitudinal fin 9A, 10A of the working bit 2 in order to rotatably secure said working bit 2 relative to said gripping handle 1 about the longitudinal axis X-X'. The plane formed by the main longitudinal slot 8 advantageously including the longitudinal axis X-X' and being advantageously orthogonal to the parting plane $P_j$, the appended fins 9A, 10A thereby extending preferably along said parting plane $P_j$, as illustrated in the figures, in order to form a «T»-shaped receiving orifice 4. Alternatively, the longitudinal slots 8, 9, 10 of the receiving orifice 4 may be for example disposed in a «Y»-like fashion. The receiving orifice 4 may also present more longitudinal fins, in order to present a cross-like, or a star-like shape. The use of main and appended slots may also apply in the preferred case represented in FIGS. 11 to 13, these slots then being orthogonal along the orthogonal axis Z-Z' and non-longitudinal along the longitudinal axis X-X' (not illustrated in the Figures).

Similarly, for the alternative variant of the invention illustrated for example in FIGS. 11 to 13, the receiving orifice 4 presents a section the shape of which allows blocking the rotation of the working bit 2 relative to said gripping handle 1 about the orthogonal axis Z-Z', while enabling the sliding of said working bit 2 relative to the gripping handle 1 along the orthogonal axis Z-Z'. Thus, according to this configuration, the receiving orifice 4 allows substantially only one degree of freedom to the working bit 2 when the latter is inserted within said receiving orifice 4.

Preferably, the receiving orifice 4 forms a beveled female recess 25, for example a hexagonal recess, which is designed to cooperate with a corresponding beveled male form 26 of the working bit 2 in order to rotatably secure said working bit 2 relative to said gripping handle 1 about the orthogonal axis Z-Z' (as illustrated in FIGS. 11 to 13), ore respectively about the longitudinal axis X-X' according to a possible variant (which is not represented in the figures).

Regardless of the shape of the receiving orifice 4, the working bit 2 presents a corresponding adapted shape, so that it could be inserted in said receiving orifice 4.

Advantageously, these preferred shapes of the receiving orifice 4 allow reducing the clearance required for the proper sliding of the working bit 2 within said receiving orifice 4, so that the assembly of said working bit 2 with the gripping handle 1 is particularly accurate and reliable.

For the preferred case represented in FIGS. 1 to 3, the receiving orifice 4 thereby presenting three longitudinal slots 8, 9, 10 or more, it is henceforth possible to insert therein a working bit 2 presenting a smaller number of corresponding longitudinal fins. In particular, it is advantageously possible to consider the insertion in the receiving orifice 4 of a working bit 2 presenting only two, or one single longitudinal fin. As example, it will be possible to insert working bits 2 such as those represented in FIGS. 9 and 10, each including only the two appended longitudinal fins 9A, 10A, and being devoid of the main fin 8A, in particular in the case where such working fins 2 are intended to form with the gripping handle a surgical tool which is not particularly intended to undergo a rotation about the longitudinal axis X-X'. Advantageously, such working bits will respectively form the wires setting guide 2B and the drill guide 2C, for example for setting a staple. In this preferred case, the working bit 2, and in particular the appended longitudinal fins 9A, 10A may be fitted with adherence means 11 designed so that, said working bit 2 being introduced in the receiving orifice 4, the adherence means 11 allow blocking or at least hardening the sliding of said working bit 2 within said receiving orifice 4, so as to secure the gripping handle 1 with said working bit 2. For example, such adherence means 11 may be formed by godroons, or nubs, disposed on the edge or the ridge of the appended longitudinal fins 9A, 10A, as illustrated in FIGS. 9 and 10.

Regardless of the considered variant of the invention, preferably, the receiving orifice 4 presents a sliding end-of-travel stop designed to stop the translation of the working bit 2 along the longitudinal axis X-X', or respectively along the orthogonal axis Z-Z', when the latter is inserted in said receiving orifice 4 at a determined depth. For example, the sliding end-of-travel stop is formed by the contour of the inlet 12 of the receiving orifice 4, against which lugs 13 or nubs of the working bit 2 (as illustrated in FIG. 8), for example disposed on at least one, or on both, of the appended longitudinal fins 9A, 10A, are intended to abut. Alternatively, the end-of-travel stop is formed by the bottom of the receiving orifice 4 (not illustrated). This preferred configuration allows further enhancing the accuracy of mounting of the working bit 2 within the receiving orifice 4.

The gripping handle 1 of the invention comprises a lever 14 for blocking the sliding of the working bit 2 in the receiving orifice 4.

The blocking lever 14 allows the surgeon to block or unblock the sliding of the working bit in the receiving orifice 4, for example by a simple pressure on said lever 14. By suppressing at least the translational degree of freedom along the longitudinal axis X-X' of the working bit 2 relative to the main body 3 of the gripping handle 1, the blocking lever 14 allows securing said working bit 2 with said gripping handle 1, so as to form the surgical tool. It also allows releasing again said translational degree of freedom of the working bit 2 relative to the main body 3 in order to release said working bit 2 of the gripping handle 1.

Advantageously, the presence of the blocking lever 14 allows realizing a very smooth receiving orifice 4, with a minimal clearance, so as to make the insertion of the working bit 2 particularly easy. The longitudinal force exerted on the working bit 2 is then advantageously taken on totally or partially by the blocking lever 14, optionally associated to the sliding end-of-travel described hereinbefore. Thus, the placement and the position holding of the working bit 2 are particularly accurate and solid, so that the formed surgical tool is quite reliable while being practical.

According to the invention, the blocking lever 14 is rotatably mounted on the main body 3 about an axis of rotation Y-Y' so as to be able to tilt between:
- a blocking orientation in which said lever blocks the sliding of the working bit 2 (represented in FIG. 1),
- a release orientation in which it enables the sliding of the working bit 2 in the receiving orifice 4.

The blocking lever 14 of the invention is designed to adopt a tilting motion about the axis of rotation Y-Y', so that for example moving one of its ends downward allows moving the other end upward, and vice versa, during a rotation about the axis of rotation Y-Y'. Preferably, the blocking lever 14 extends between an end 17 for blocking the working bit 2 and an end 18 for manually maneuvering said blocking lever 14. Thus, preferably, an action by the surgeon on the maneuvering end 18 allows making the blocking lever 14 tilt, such a motion being transmitted by the body of said blocking lever 14 to the blocking end 17. Preferably, the axis of rotation Y-Y' is therefore located between the blocking end 17 and said maneuvering end 18. Preferably, a pressure on the maneuvering end 18 allows making the blocking lever 14 tilt toward its release orientation. Of course, alternatively, without departing from the scope of the invention, raising the maneuvering end 18 allows making the blocking lever 14 tilt toward its release orientation.

Preferably, from the blocking end 17 to the maneuvering end 18, the lever is disposed substantially parallel to the longitudinal axis X-X', in the blocking orientation or in the release orientation. Advantageously, the axis of rotation Y-Y' is substantially orthogonal (as illustrated in FIGS. 11 to 13), or substantially orthoradial (as illustrated in FIGS. 1 to 3) with respect to the longitudinal axis X-X'.

By «orthoradial», is meant that the axis of rotation Y-Y' is substantially coaxial with a tangent to the circle which is itself coaxial with the longitudinal axis X-X'. Thus, the blocking lever 14 can be actuated by the surgeon when the latter rotates said blocking lever 14 for example by a few degrees or tens degrees, about the axis of rotation Y-Y'. In the preferred case of FIGS. 11 to 13, the axis of rotation Y-Y' is advantageously parallel to the orthogonal axis Z-Z', so that the three axes X-X', Y-Y' and Z-Z' geometrically belong to the parting plane $P_j$.

According to the invention, the release orientation of the lever 14 allows releasing the sliding of the working bit 2 in particular in the case where the sliding of the latter was initially blocked by said lever 14. In the release orientation, the working bit 2 can perfectly slide along the longitudinal axis X-X', or respectively along the orthogonal axis Z-Z', in the receiving orifice 4, and be freely extracted therefrom, or on the contrary freely inserted therein.

In the blocking orientation, a portion or an end of the lever preferably comes into contact with the working bit 2 or a portion of the latter, in order to block the sliding of said working bit 2 in the receiving orifice 4. Preferably, blocking the sliding of the working bit 2 by the blocking lever 14 cannot be performed unless the working bit 2 is inserted within the receiving orifice until substantially abutting axially against the end-of-travel stop, or at least until reaching a position close to the position in which it abuts against the end-of-travel stop. Advantageously, this «end-of-travel» position corresponds to the relative position of the working bit 2 and of the main body 3 when the surgical tool is assembled.

Consequently, releasing or blocking the working bit 2 is particularly easy, to the extent that a simple pressure on, or a motion, of said blocking lever 14 allows releasing and/or blocking said working bit 2 within the gripping handle 1.

Preferably, as illustrated in the figures, the gripping handle 1 comprises a groove 19 formed in the main body 3 and extending longitudinally, the blocking lever 14 being disposed within said groove 19 so as not to surpass the external contour of the main body 3 over at least one-third the length of said blocking lever 14 when the latter is in the blocking orientation.

By «external contour», is meant the virtual contour of the main body 3, considered as if the latter was devoid of any notch, cavity, groove, or furrow. Preferably, the external contour of the main body 3 presents the shape of an ellipsoid of revolution about the longitudinal axis X-X'. Preferably, the groove 19 forms a furrow, for example radial and longitudinal with respect to the longitudinal axis X-X' of the main body 3, and within which all or part of the blocking lever 14 is fitted, or integrated.

According to this preferred configuration, the blocking lever 14 does not protrude, or barely protrudes, from the main body 3, so that it does not constitute an obstacle to the ergonomics of gripping of the main body 3 by the surgeon. Preferably, in the blocking orientation, the blocking lever 14 follows the external curve of the contour of the groove 19, and therefore of the main body 3, for example from the blocking end 17 to half, two-thirds, or three-quarters the length of said blocking lever 14 in the direction of the maneuvering end 18. Therefore, on the contrary, the latter does protrude from the main body 3 so as to be accessible for maneuvering. Advantageously, the gripping handle 1 comprises a maneuvering concavity 20 formed in the main body 3, within which the maneuvering end 18 of the blocking lever 14 protrudes. Thus, the blocking lever 14 protrudes from the maneuvering concavity 20, preferably in the vicinity of its maneuvering end 18, in order to be easy to maneuver. Preferably, the blocking lever 14 protrudes sufficiently from the maneuvering concavity 20 so as not to surpass the external contour of the main body 3. Such a design makes the gripping handle 1 perfectly comfortable and ergonomic, while allowing an easy maneuvering of the blocking lever 14.

The gripping handle 1 of the invention also comprises an elastic pivot 15, 16 by which the blocking lever 14 is rotatably mounted on the main body 3, the elastic pivot 15, 16 being designed to bring, by itself, the blocking lever 14 back in the blocking orientation when the latter is in the release orientation. The elastic pivot 15, 16 combines the functions of:
  pivot linkage between the blocking lever 14 and the main body 3 about the axis of rotation Y-Y',
  means for automatically returning the blocking lever 14 toward its blocking orientation.

In this manner, when the working bit 2 is in the adequate position within the receiving orifice 4, and is in particular in the vicinity of the end-of-travel position, the blocking lever 14 orientates itself in the blocking position in order to block the sliding of the working bit 2. Thus, securing the working bit 2 with the gripping handle 1 is quite easy.

Preferably, the blocking lever 14 returning, by itself, in the blocking orientation, it remains in the blocking orientation in the absence of action or maneuver of the surgeon on said blocking lever 14. Preferably, the working bit 2 and the blocking lever 14 are shaped so that the insertion of the working bit 2 in the receiving orifice 4 results in a modification of the orientation of the blocking lever 14 toward its release position, until the working bit 2 is inserted deep enough in the receiving orifice 4, until reaching a so-called «end-of-travel» position in which the blocking lever 14 tilts by itself under the action of the elastic pivot 15, 16 toward its blocking orientation, and therefore automatically blocks the sliding of the working bit 2 without any action or maneuver of the surgeon on said blocking lever 14.

Preferably, the blocking lever 14 is provided with a slope 23 for driving said blocking lever 14 toward its release orientation, said drive slope 23 being to this end designed to be driven by a slope 24 for lifting the working bit 2 during the insertion of said working bit 2 (as illustrated in FIGS. 5 to 7). Preferably, the lifting slope 24 is formed by an extreme edge of the main longitudinal fin 8A of the working bit (as illustrated for example in FIG. 4).

In order to release the working bit 2, the surgeon preferably maneuvers the blocking lever 14 so as to orientate it toward its release orientation, which releases the working bit 2, and allows making it slide out of the receiving orifice 4.

Thus, the mounting and the dismount of the surgical tool formed by the gripping handle 1 of the invention is particularly rapid and easy.

According to a major feature of the invention, the main body 3, the blocking lever 14 and the elastic pivot 15, 16 are integral with each other so as to form a one single-piece part. In this case, the gripping handle 1 of the invention constitutes a single monobloc part, advantageously made of one single matter processed so as to obtain at the same time the main body 3, the blocking lever 14 and the elastic pivot 15, 16. In particular, the gripping handle 1 of the invention is not the result of the assembly of several parts. This design allows the gripping handle 1 of the invention to be particularly easy to manufacture, for example manufactured by molding a preform of the gripping handle 1, and machining said preform of the gripping handle 1 in order to form at the same time the main body 3, the elastic pivot 15, 16 and the blocking lever 14. Preferably, the gripping handle 1 is manufactured through one single molding operation, that is to say that the material intended to form the whole gripping handle 1 is inserted in a mold, for example by injection or by casting, and the gripping handle is formed and finished when opening the mold. Thus, for its manufacture, the gripping handle 1 advantageously does not necessitate any machining complementary to molding.

The material used for such a manufacture should be chosen so as to be sufficiently elastic for the formation of the elastic pivot 15, 16, and at the same time, sufficiently resistant so that the main body 3 allows a solid and safe gripping of the surgical tool. In addition, the used material is preferably moldable or injectable in order to enable the manufacture of the gripping handle 1 according to the previous arrangements. Finally, the material should advantageously enable its sterilization, to the extent that the gripping handle will be used for surgical purposes. Consequently, the gripping handle 1 is preferably realized in a one single-piece part from a polymer material, for example PEEK, such a material being advantageously compliant with all the previous criteria. Alternatively, a metallic alloy such as stainless steel or a composite material may be used.

In this manner, the polymers being generally relatively inexpensive to implement, it is possible to consider realizing a disposable and/or recyclable, and/or one-use gripping handle 1. For example, the gripping handle may be provided in the form of a sterilized kit, the kit also comprising working bits 2, disposable or not, the kit being usable for a given surgical operation, and being intended to be withdrawn or recycled at the end of said surgical operation. In this manner, the proper sterilization of the surgical environment is ensured.

Preferably, the axis of rotation. Y-Y' is located between the blocking end 17 and said maneuvering end 18 so as to be closer to the blocking end 17 than the maneuvering end 18. Thus, with an equal rotational torque about the axis of rotation Y-Y' of the blocking lever 14, it is necessary to exert a lighter maneuver on the maneuvering end 18 than on the blocking end 17, in order to modify the orientation of said blocking lever 14 against the elasticity of the elastic pivot 15, 16. Thus, maneuvering the blocking lever 14 is particularly easy, and its blocking of the working bit 2 is therefore particularly strong. Preferably, the axis of rotation Y-Y' is located at about one-third the length of the blocking lever 14 from the blocking end 17, as illustrated in the figures.

Advantageously, the elastic pivot 15, 16 links the blocking lever 14 to at least one wall of the groove 19.

More specifically, as illustrated in the figures, the blocking lever 14 advantageously forms a blade extending substantially orthogonally to the axis of rotation Y-Y', the elastic pivot 15, 16 being formed by two substantially semi-cylindrical pivot elements 15, 16, the height axis of which is formed by the axis of rotation Y-Y', said pivot elements being materialized on either side of the blocking lever 14 so as to link the latter to two distinct walls of the groove 19. Preferably, these walls are parallel and face each other, the blocking lever 14 being disposed therebetween. Thus, the blocking lever 14 is symmetrically positioned in the main body 3, which is particularly solid and durable. Thus, the elastic pivot 15, 16 advantageously presents an undercut with respect to the parting plane $P_j$ so as to allow realizing it by molding at the same time as the main body and the blocking lever 14. In turn, the receiving orifice 4 is preferably set back in a direction coaxial with the longitudinal axis X-X' so as to allow modeling it by a drawer of a mold with drawers during the molding operation.

Preferably, the main longitudinal slot 8 of the receiving orifice 4 is substantially aligned in the extension of the blocking lever 14, the main longitudinal fin 8A being designed to come into contact with said blocking lever 14, and in particular with the blocking end 17 so as to allow blocking said working bit 2 by said blocking lever 14. Thus, the main longitudinal slot 8, and/or the blocking lever 14, and/or the furrows 5, and/or the groove 19 are preferably orientated along planes parallel to each other, which are themselves orthogonal to the parting plane $P_j$, which facilitates the manufacture of the gripping handle 1, and in particular the possible molding steps.

Preferably, the blocking lever 14 is designed to mechanically block the sliding of the working bit 2 by form-fitting between the blocking lever 14 and the working bit 2. Thus, such a configuration allows an accurate position holding of the working bit 2 within the receiving orifice 4. Nonetheless, the blocking lever 14 may simply blocks the working bit 2 by adherence.

Advantageously, the elastic pivot 15, 16 provides a force for returning the blocking lever 14 toward its blocking orientation when said blocking lever 14 is brought away from its blocking orientation, the blocking force being applied on the working bit 2 via the blocking lever 14, the latter being provided with a surface 27 for bearing the return force (as illustrated in FIG. 7) allowing the blocking lever 14 to press the working bit 2 in the direction of the longitudinal axis X-X' under the action of the elastic pivot 15, 16 against an end-of-travel stop, when said blocking lever 14 mechanically blocks the sliding of said working bit 2.

Preferably, the load-bearing surface 27 is designed to interact with a receiving surface 28 of the working bit 2, which are designed to be brought into contact with each other so as to slip against each other. Preferably, the load-bearing surface 27 and the receiving surface 28 are substantially parallel to each other when the working bit 2 is inserted in the receiving orifice 4, and are preferably inclined with respect to the longitudinal axis X-X', with respect to the parting plane $P_j$, for example about an axis orthoradial to the longitudinal axis X-X'.

The sliding contact of the load-bearing surface 27 against the receiving surface 28 allows transmitting to the working bit 2 a component coaxial to the longitudinal axis X-X' of the return force provided by the elastic pivot 15, 16, so as to allow pressing said working bit 2 against an end-of-travel stop under the action of said elastic pivot 15, 16 transmitted via said blocking lever 14.

Advantageously, the end-of-travel stop is an axial stop, allowing stopping the translation of the working bit 2 along the longitudinal axis X-X', as described hereinbefore.

Preferably, as illustrated in the figures, the blocking lever 14 is provided with a blocking latch 21 designed to be inserted, or to be inserted by itself, in a blocking notch 22 of the working bit 2 in order to block the sliding of the latter when the blocking lever 14 is in the blocking orientation. Preferably, the blocking notch 22 is carried by the main longitudinal fin 8A. Advantageously, the blocking latch 21 also forms the slope 23 for driving the blocking lever 14 in rotation toward its release orientation. Of course, the reverse arrangement may be advantageously adopted, in which the working bit 2 would include a blocking latch and the gripping handle would include a corresponding blocking notch.

Preferably, as illustrated in FIG. 7, a portion of the external contour of the blocking latch 21, in particular the blocking end 17 of the blocking lever 14, forms the load-bearing surface 27. Similarly, a portion of the external contour of the blocking notch 22 forms the receiving surface 27. In addition, the blocking latch 21 advantageously comprises a retaining surface 29, intended to come into contact with a matching surface 30 of the working bit 2, so as to mechanically block the sliding of said working bit 2 out of the receiving orifice 4.

Preferably, the load-bearing surface 27 is also the drive slope 23.

Thus, the blocking latch 21 and the blocking notch 22 advantageously have a matching and complementary shape.

The invention also concerns, as such, a surgical tool kit comprising a gripping handle 1 as described hereinbefore, as well as at least one removable working bit 2, preferably two removable working bits 2 having different functions.

By «different function», is meant that the two working bits 2 allow forming with the gripping handle 1 respectively a first surgical tool and a second surgical tool the function of which will be different from the first surgical tool, that is to say that said surgical tools are intended to perform distinct and non-similar actions, or still interact differently with the operative medium and with the body of the patient. For example, working bits 2 with different functions allow screwing or unscrewing respectively a first screw with a first head imprint, and a second screw with a second head imprint different from the first head imprint.

Preferably, the working bits 2 correspond to those described hereinbefore. Advantageously, in accordance with the foregoing, one of the working bits 2 is formed by a screwdriver bit 2A, another one of the working bits 2 being formed by a drill guide 2C, for example for setting osteosynthesis staples and/or wires, or a guide for setting wires 2B.

Advantageously, the surgical tool kit comprises the wires, the screws, the staples, and additional working bits 2, for example:
- at least one second screwdriver working bit 2, which allows screwing a screw the imprint or the nominal diameter of which differs from the screw which can be screwed by the screwdriver bit 2A, and/or
- a working bit 2 for gripping the staples, and/or
- a working bit 2 for impacting the staples in a bone of the patient, and/or
- a working bit 2 for impacting the wires in a bone of the patient, and/or
- a working bit 2 for drilling holes in a bone of the patient.

Preferably, the surgical tool kit is disposable and/or intended for a single use, and is preferably contained in a package in a sterilized atmosphere.

The invention further concerns, as such, a method for manufacturing a gripping handle 1 as described hereinbefore. According to the invention, the manufacturing method comprises one single molding step during which the gripping handle 1 is made in one single piece. In other terms, the manufacturing method of the invention allows realizing the gripping handle 1 as described hereinbefore, in one single operation, without any other finishing operation such as machining or the same. Advantageously, the matter intended to be molded during the manufacturing method is a polymer.

Preferably, the manufacture of the gripping handle is carried out in the following manner:
- pouring or casting or injecting the material intended to form the gripping handle 1 in a manufacturing machine formed by a mold, for example a mold with drawers, so that the material is modeled by the manufacturing machine, in this case by the mold,
- opening the mold once the material has been modeled, the latter forming the gripping handle 1 in its final shape.

Finally, the invention concerns as such a machine (not illustrated in the figures) for manufacturing a gripping handle 1 as described hereinbefore, and allowing implementing the manufacturing method described hereinbefore.

Preferably, the manufacturing machine of the invention comprises a mold comprising a first molding cavity, a second molding cavity and at least one first drawer, which are intended to form a closed space in which a material intended to form the gripping handle 1 is intended to be cast. Preferably, when the material is cast in the mold:
- the first mold cavity together with the second mold cavity are designed to model the material in order to form, at least partially, the main body 3, the blocking lever 14 and the elastic pivot 15, 16,
- the first drawer being designed to form the receiving orifice 4 within the main body 3.

Thus, the manufacturing machine of the invention advantageously forms a mold with drawers.

In the context of the invention, «modeling» means giving shape to the matter by molding.

Advantageously, the first cavity is designed to model the portion of the gripping handle 1 rising from the parting plane $P_j$ in the first space direction, the second cavity is designed to model the portion of the gripping handle 1 rising from the parting plane $P_j$ in the second space direction opposite to said first space direction.

Preferably, the manufacturing machine also comprises a second drawer designed to form, with the first drawer, the receiving orifice 4 within the main body 3, the first drawer serving to form a first portion of the receiving orifice 4 extending from the distal end 6, the second drawer serving to form a second portion of the receiving orifice 4 extending from the proximal end 7.

When the mold is closed, that is to say when the first cavity is attached against the second cavity, the drawers are preferably designed to extend along the parting plane $P_j$ so as to form the receiving orifice 4.

Thus, the manufacturing machine of the invention allows realizing the gripping handle 1 of the invention in one single molding operation, preferably without any complementary machining, so that the gripping handle 1 of the invention is particularly easy, rapid, and inexpensive to manufacture.

POSSIBILITY OF INDUSTRIAL APPLICATION

The invention finds its industrial application in the design, the manufacture and the use of gripping handles designed to receive a removable working bit in order to form a surgical tool with the latter, surgical tools kits comprising such a gripping handle, and manufacturing machines intended for the implementation of a method for manufacturing such gripping handles.

The invention claimed is:

1. A gripping handle (1) designed to receive a removable working bit (2) in order to form a surgical tool with the removable working bit (2), said gripping handle (1) comprising:
- a main body (3) extending along a longitudinal axis (X-X') between a proximal end (7) and a distal end (6);
- a receiving orifice (4) formed within the main body (3) and being designed to slidingly receive the working bit (2);
- a lever (14) for blocking the sliding of the working bit (2) in the receiving orifice (4), the blocking lever (14) being rotatably mounted on the main body (3) about an axis of rotation (Y-Y') so as to be able to tilt between:
- a blocking orientation in which said lever blocks the sliding of the working bit (2), and
- a release orientation in which it enables the sliding of the working bit (2) in the receiving orifice (4); and
- an elastic pivot (15, 16) by which the blocking lever (14) is rotatably mounted on the main body (3), the elastic pivot (15, 16) being designed to bring, by itself and when the blocking lever (14) is in the release orientation, the blocking lever (14) back in the blocking orientation, wherein the main body (3), the blocking lever (14) and the elastic pivot (15, 16) are integral with each other so as to form a one single-piece part.

2. The gripping handle (1) according to claim 1, wherein the blocking lever (14) extends between an end (17) for blocking the working bit (2) and an end (18) for manually maneuvering said blocking lever (14), the axis of rotation (Y-Y') being located between the blocking end (17) and said maneuvering end (18) so as to be closer to the blocking end (17) than the maneuvering end (18).

3. The gripping handle (1) according to claim 2, wherein the axis of rotation (Y-Y') is located at about one-third the length of the blocking lever (14) from the blocking end (17).

4. The gripping handle (1) according to claim 2, further comprising a maneuvering concavity (20) formed in the main body (3), within which the maneuvering end (18) of the blocking lever (14) protrudes.

5. The gripping handle (1) according to claim 1, further comprising a groove (19) formed in the main body (3) and extending longitudinally, the blocking lever (14) being disposed within said groove (19) so as not to surpass the external contour of the main body (3) over at least one-third the length of said blocking lever (14) when the blocking lever (14) is in the blocking orientation.

6. The gripping handle (1) according to claim 1, wherein the elastic pivot (15, 16) links the blocking lever (14) to at least one wall of the groove (19).

7. The gripping handle (1) according to claim 6, wherein the blocking lever (14) forms a blade extending substantially orthogonally to the axis of rotation (Y-Y'), the elastic pivot (15, 16) being formed by two substantially semi-cylindrical pivot elements the height axis of which is formed by the axis of rotation (Y-Y'), said pivot elements being disposed on either side of the blocking lever (14) so as to link the blocking lever (14) to two distinct walls of the groove (19).

8. The gripping handle (1) according to claim 1, wherein the blocking lever (14) is designed to mechanically block the sliding of the working bit (2) by form-fitting between the blocking lever (14) and the working bit (2).

9. The gripping handle (1) according to claim 8, wherein the elastic pivot (15, 16) provides a force for returning the blocking lever (14) toward its blocking orientation when said blocking lever (14) is brought away from its blocking orientation, the blocking force being applied on the working bit (2) via the blocking lever (14), the blocking lever (14) being provided with a surface (27) for bearing the return force allowing the blocking lever (14) to press the working bit (2) in the direction of the longitudinal axis (X-X') under the action of the elastic pivot (15, 16) against an end-of-travel stop, when said blocking lever (14) mechanically blocks the sliding of said working bit (2).

10. The gripping handle (1) according to claim 8, wherein the blocking lever (14) is provided with a blocking latch (21) designed to be inserted in a blocking notch (22) of the working bit (2) in order to block the sliding of the working bit (2) when the blocking lever (14) is in the blocking orientation.

11. The gripping handle (1) according to claim 1, wherein the receiving orifice (4) is formed within the main body (3) from the distal end (6).

12. The gripping handle (1) according to claim 11, wherein the receiving orifice (4) is designed to receive the working bit (2) sliding along the longitudinal axis (X-X'), so as to form an axial surgical tool.

13. The gripping handle (1) according to claim 12, wherein the receiving orifice (4) presents a section the shape of which allows blocking the rotation of the working bit (2) relative to said gripping handle (1) about the longitudinal axis (X-X'), while enabling the sliding of said working bit (2) relative to the gripping handle (1) along the longitudinal axis (X-X').

14. The gripping handle (1) according to claim 13, wherein the receiving orifice (4) presents at least one main longitudinal slot (8) extending over at least a portion of the length of said receiving orifice (4), the main longitudinal slot (8) being designed to cooperate with a main longitudinal fin (8A) of the working bit (2) in order to rotatably secure said working bit (2) relative to said gripping handle (1) about the longitudinal axis (X-X').

15. The gripping handle (1) according to claim 14, wherein the receiving orifice (4) also presents two appended longitudinal slots (9, 10) disposed symmetrically with respect to a plane formed by the main longitudinal slot (8), the appended longitudinal slots (9, 10) being designed to cooperate each with an appended longitudinal fin (9A, 10A) of the working bit (2) in order to rotatably secure said working bit (2) relative to said gripping handle (1) about the longitudinal axis (X-X').

16. The gripping handle (1) according to claim 14, wherein the main longitudinal slot (8) is substantially aligned in the extension of the blocking lever (14), the main, longitudinal fin (8A) being designed to come into contact with said blocking lever (14) so as to allow blocking said working bit (2) by said blocking lever (14).

17. The gripping handle (1) according to claim 1, wherein the receiving orifice (4) is formed within the main body (3), so as to open from the outer surface of the main body (3), between the distal end (6) and the proximal end (7).

18. The gripping handle (1) according to claim 17, wherein the receiving orifice (4) is designed to receive the working bit (2) sliding along an orthogonal axis (Z-Z') orthogonal to the longitudinal axis (X-X') so as to form a «T»-shaped surgical tool.

19. The gripping handle (1) according to claim 18, wherein the receiving orifice (4) presents a section the shape of which allows blocking the rotation of the working bit (2) relative to said gripping handle (1) about the orthogonal axis (Z-Z'), while enabling the sliding of said working bit (2) relative to the gripping handle (1) along the orthogonal axis (Z-Z').

20. The gripping handle (1) according to claim 19, wherein the receiving orifice (4) forms a beveled female recess which is designed to cooperate with a corresponding beveled male form of the working bit (2) in order to rotatably secure said working bit (2) relative to said gripping handle (1) about the orthogonal axis (Z-Z').

21. The gripping handle (1) according to claim 1, wherein the receiving orifice (4) presents a sliding end-of-travel stop designed to stop the translation of the working bit (2) along the longitudinal axis (X-X').

22. The gripping handle (1) according to claim 1, wherein the gripping handle (1) forms a screwdriver handle.

23. The gripping handle (1) according to claim 1, wherein the gripping handle (1) is a one single-piece part from a polymer material.

24. The gripping handle (1) according to claim 23, wherein the gripping handle (1) is manufactured through one single molding operation.

25. The gripping handle (1) according to claim 1, wherein the axis of rotation (Y-Y') is substantially orthogonal, or substantially orthoradial with respect to the longitudinal axis (X-X').

26. A surgical tool kit comprising the gripping handle (1) according to claim 1 and at least one removable working bit (2) or two removable working bits (2) having different functions.

27. The surgical tool kit according to claim 26, wherein one of the working bits (2) is formed by a screwdriver bit (2A), another one of the working bits (2) being formed by a drill guide (2C) or a guide for setting wires (2B).

* * * * *